US012573483B2

(12) United States Patent
Lowrey et al.

(10) Patent No.: US 12,573,483 B2
(45) Date of Patent: *Mar. 10, 2026

(54) SYSTEMS AND METHODS FOR PROCESSING DIABETES THERAPY DATA

(71) Applicant: Tandem Diabetes Care, Inc., San Diego, CA (US)

(72) Inventors: Larkin Lowrey, Naples, FL (US); Beau Randall, Denver, CO (US); Tobias Lohse, Chicago, IL (US); Shaun Buchanan, Hampstead, NC (US); Xavier de Anda, San Diego, CA (US); Jacob Kearns, San Diego, CA (US)

(73) Assignee: Tandem Diabetes Care, Inc., San Diego, CA (US)

( * ) Notice: Subject to any disclaimer, the term of this patent is extended or adjusted under 35 U.S.C. 154(b) by 197 days.

This patent is subject to a terminal disclaimer.

(21) Appl. No.: 18/519,344

(22) Filed: Nov. 27, 2023

(65) Prior Publication Data

US 2024/0087698 A1 Mar. 14, 2024

Related U.S. Application Data

(63) Continuation of application No. 17/729,464, filed on Apr. 26, 2022, now Pat. No. 11,830,595.

(60) Provisional application No. 63/179,819, filed on Apr. 26, 2021.

(51) Int. Cl.
*G16H 15/00* (2018.01)
*G06F 3/04817* (2022.01)
*G06F 3/04842* (2022.01)
*G16H 20/00* (2018.01)

(52) U.S. Cl.
CPC ......... *G16H 15/00* (2018.01); *G06F 3/04817* (2013.01); *G06F 3/04842* (2013.01); *G16H 20/00* (2018.01)

(58) Field of Classification Search
CPC .... G16H 15/00; G16H 20/00; G06F 3/04817; G06F 3/04842; G06T 11/206
See application file for complete search history.

(56) References Cited

U.S. PATENT DOCUMENTS

| | | | |
|---|---|---|---|
| 9,238,100 B2 | 1/2016 | Kruse et al. | |
| 9,335,910 B2 | 5/2016 | Farnan et al. | |
| 9,715,327 B2 | 7/2017 | Rosinko et al. | |
| 9,814,835 B2 | 11/2017 | Kruse et al. | |
| 10,430,043 B2 | 10/2019 | Rosinko et al. | |
| 10,434,253 B2 | 10/2019 | DiPerna et al. | |
| 10,653,834 B2 | 5/2020 | Kruse et al. | |
| 10,994,077 B2 | 5/2021 | Rosinko | |
| 11,135,362 B2 | 10/2021 | DiPerna et al. | |
| D938,457 S | 12/2021 | Rosinko et al. | |
| 11,285,263 B2 | 3/2022 | DiPerna et al. | |

(Continued)

OTHER PUBLICATIONS

Application and File history for U.S. Appl. No. 17/517,885, filed Nov. 3, 2021. Inventors: Juster.

*Primary Examiner* — Cao H Nguyen
(74) *Attorney, Agent, or Firm* — Morgan, Lewis & Bockius LLP

(57) ABSTRACT

Disclosed herein are system and methods for organizing diabetes therapy data from different devices and across time changes that enable user analysis and visualization in a way that incorporates the changes in user time.

20 Claims, 6 Drawing Sheets

(56) References Cited

U.S. PATENT DOCUMENTS

| | | | |
|---|---|---|---|
| 11,488,549 B2 | 11/2022 | Blomquist et al. | |
| 11,580,918 B2 | 2/2023 | Blomquist et al. | |
| 11,607,492 B2 | 3/2023 | Rosinko et al. | |
| 11,694,794 B2 | 7/2023 | Farnan et al. | |
| 2011/0152770 A1 | 6/2011 | DiPerna et al. | |
| 2013/0283196 A1 | 10/2013 | Farnan et al. | |
| 2013/0331778 A1 | 12/2013 | Kruse et al. | |
| 2013/0332874 A1 | 12/2013 | Rosinko et al. | |
| 2016/0121047 A1 | 5/2016 | Kruse et al. | |
| 2016/0199571 A1 | 7/2016 | Rosinko et al. | |
| 2016/0271325 A1 | 9/2016 | Farnan et al. | |
| 2017/0056590 A1 | 3/2017 | DiPerna et al. | |
| 2017/0116373 A1* | 4/2017 | Ginsburg | G16H 50/70 |
| 2017/0300206 A1 | 10/2017 | Rosinko et al. | |
| 2018/0064873 A1 | 3/2018 | Kruse et al. | |
| 2018/0089376 A1* | 3/2018 | Tucker | G06F 16/9535 |
| 2018/0361060 A9 | 12/2018 | Rosinko | |
| 2019/0259485 A1 | 8/2019 | Blomquist et al. | |
| 2019/0321552 A1 | 10/2019 | DiPerna et al. | |
| 2020/0012401 A1 | 1/2020 | Rosinko et al. | |
| 2020/0016335 A1 | 1/2020 | DiPerna et al. | |
| 2020/0101226 A1 | 4/2020 | Rosinko et al. | |
| 2021/0012875 A1 | 1/2021 | Blomquist et al. | |
| 2022/0001106 A1 | 1/2022 | DiPerna et al. | |
| 2022/0084664 A1* | 3/2022 | Ginsburg | G16H 15/00 |
| 2022/0139522 A1 | 5/2022 | Juster | |

* cited by examiner

SYSTEMS AND METHODS FOR PROCESSING DIABETES THERAPY DATA

CROSS REFERENCE TO RELATED APPLICATIONS

This application is a continuation of U.S. patent application Ser. No. 17/729,464 filed Apr. 26, 2022, which claims the benefit of U.S. Provisional Application No. 63/179,819 filed Apr. 26, 2021, each of which is hereby fully incorporated herein by reference.

FIELD OF THE INVENTION

The present invention relates generally to diabetes therapy and, more particularly, to presentation of therapy data for diabetes therapy on a user interface.

BACKGROUND OF THE INVENTION

People with diabetes can treat the disease in a number of different ways, including with insulin pumps, insulin pens and regular injections with a syringe. Regardless of the method of treatment it is important for the user to be able to track and review data relating to therapy to aid the user in better managing his/her diabetes. A number of different data management software programs, mobile applications, etc. have therefore been developed that enable a user to review therapy data.

Diabetes therapy data is frequently sequenced in the order events occur with a reference time used to understand the time relationship between events. Diabetes therapy can involve multiple devices that may record data and events and eventually the data from the multiple devices must be complied in a central location. However, the multiple devices may use difference references times and the central location also may not be able to receive all events from all devices in real time, which can complicate organization and presentation of the data in an accurate and useable format for the user.

It is therefore important to align the dates and times of the data from the multiple devices in a manner that is relevant to the user. In addition, the date and time relevant to the user can be impacted by various time changes, daylight savings time, travel through time zones, clock corrections etc., which can further complication accurate and useful presentation of the data.

SUMMARY

Disclosed herein are system and methods for organizing diabetes therapy data from different devices and across time changes that enable user analysis and visualization in a way that incorporates the changes in user time.

In an embodiment, a method for organizing and presenting diabetes therapy events on a graphical user interface includes obtaining data relevant to diabetes therapy from a plurality of different sources. The data relevant to diabetes therapy data can be segmented into segments for each of the plurality of sources, wherein each segment for each source represents a continuous period of data for the source and additional segments are created for each source when there has been a data disruption on the source. Segments from each source can then be aligned with segments from other sources with respect to real time. A therapy timeline can be displayed including data from one or more segments of the plurality of sources, the therapy timeline displaying aligned segments over a predetermined time period with the data from the plurality of sources overlain on the timeline at a time that events recorded by the plurality of sources occurred.

In an embodiment, a method for organizing and presenting diabetes therapy events on a graphical user interface can include obtaining data relevant to diabetes therapy from a plurality of different sources including an infusion pump. A therapy timeline can be displayed on a graphical user interface including data from the plurality of sources over a predetermined time period with the data from the plurality of devices overlain on the therapy timeline at a time that events from the plurality of devices occurred. If it is determined that a pump time was changed on the infusion pump the therapy timeline can cease displaying data at a time when the pump time was changed on the infusion pump and a time change indicator can be displayed on the therapy timeline at the time when the pump time was changed on the infusion pump. A time change therapy timeline can then be displayed on the graphical user interface, the time change therapy timeline displaying the data from the plurality of sources beginning at a time to which the pump time was changed and including a time change indicator at the time to which the pump time was changed.

The above summary is not intended to describe each illustrated embodiment or every implementation of the subject matter hereof. The figures and the detailed description that follow more particularly exemplify various embodiments.

BRIEF DESCRIPTION OF THE DRAWINGS

The invention may be more completely understood in consideration of the following detailed description of various embodiments of the invention in connection with the accompanying drawings, in which.

FIG. 3 depicts various information tiles that can be displayed on a therapy timeline graph according to embodiments.

Figure 1:
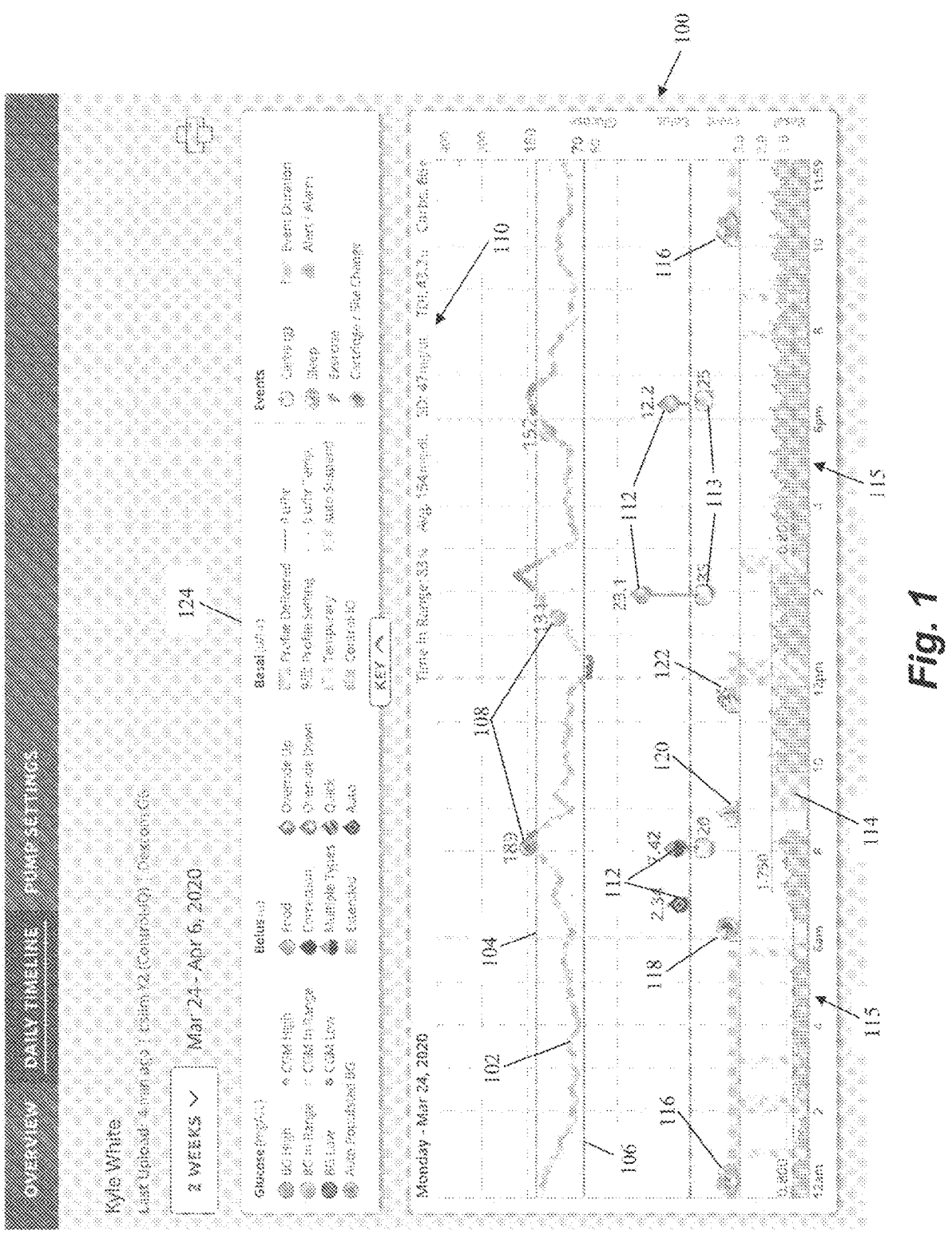
FIG. 1 depicts a therapy timeline graph according to an embodiment.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION OF THE INVENTION

The following detailed description should be read with reference to the drawings in which similar elements in different drawings are numbered the same. The drawings, which are not necessarily to scale, depict illustrative embodiments and are not intended to limit the scope of the invention.

Referring to FIG. 1, a therapy timeline graph for diabetes therapy is depicted. The data feed can be displayed on any display device, such as, for example, a tablet computer, desktop computer or laptop computer or a smartphone operating a software application that receives and displays therapy data. Diabetes therapy can be provided in any manner, including, for example, with an ambulatory infusion pump, an insulin pen and multiple daily injections.

As can be seen in FIG. 1, therapy timeline 100 can depict many different types of data on a single timeline. For example, therapy timeline 100 can include a CGM data feed 102 showing the user's glucose levels from a continuous glucose monitor over time with respect to a high glucose threshold 104 and a low glucose threshold 106. The CGM feed 102 can further include blood glucose levels 108 entered by the user when the user performs blood glucose measurements. Various calculated therapy statistics 110 can be displayed adjacent the graph, such as, for example, Time in Range (i.e., the percentage of time the user's glucose levels is between the high threshold 104 and the low threshold 106), the user's average glucose level (Avg.), the standard deviation of the user's glucose levels (SD), the total daily insulin for the user (TDI) and the number of carbs ingested by the user (Carbs).

The therapy timeline 100 can further include graphical representations of the insulin delivered to the user in the form of bolus and basal insulin deliveries. For example, bolus delivery icons 112 can include correction bolus, meal bolus and combination bolus icons (see the "KEY" 124) with the meal bolus and combination bolus icons including a corresponding meal icon 113 indicating the number of carbohydrates consumed. In the depicted embodiment, basal delivery can be indicated by both basal profile delivery 114 according to the user's stored open loop basal profile and closed loop basal delivery 115 that is continually modified based on glucose levels according to a closed loop algorithm. The timeline 100 can also display icons pertaining to various events that are relevant to therapy including, for example, sleep 116, cartridge or infusion site changes 118, pump alarms or alerts 120 and exercise 122. The KEY 124 denotes various other events and information that can be depicted on therapy timeline 100. In some embodiments, each type of data can be a distinct "layer" that can be turned on and off to enable the user to customize the data display to the user's preference. In embodiments, a layer can be turned on and off directly from the therapy timelines or, alternatively or additionally, layers can be turned and off from a separate menu.

Information relating to therapy events can be obtained by the data application from a variety of sources. For example, a user can manually enter data associated with any event. For therapy provided by ambulatory infusion pumps, smart insulin pens or any other device capable of electronic communications, the therapy device can transmit therapy data to the data application wirelessly or when a wired connection is established with, e.g., a computer. Exercise and food information can be obtained from health management applications operating on smartphones or other devices. Exercise information could further be obtained from a fitness app or directly from an activity monitoring device, such as a smartwatch. Glucose readings can be measured by a continuous glucose monitor. In various embodiments, the data application can obtain the CGM data from a third-party diabetes data management system, from an ambulatory infusion pump or other therapy device and/or directly from the CGM.

As noted above, the data and events for a therapy timeline such as the one depicted in FIG. 1 can be received from different devices having different and/or changing reference times, at different times, out of order, etc. Embodiments presented herein therefore provide for systems that organize such data in a way that allows user analysis and visualization in a relevant and useable way.

In embodiments, systems disclosed herein segment data when there is a change in time or date for a device. Additional segmentation can be performed for various reasons, such as periods of no data, hardware or software change, etc. The segmentation could be performed in a cloud system, remote system, or on the user's system where the data is presented. Segments can further be transferred between systems asynchronously and easily reorganized at the destination. Because evens within a given segment are always in order by both relative and user time, multiple segments can be ordered by either sequence, relative time or user time to enable the data to be visualized in a number of ways. The system can further enable overlapping user time periods due to a clock change to be visualized in the order the user experienced the events.

Sequencing the data as described above enables the visualization to be shown as the user experienced events. This enables an event that spans multiple time changes to be displayed while retaining accuracy of the event duration. Data can also be stored in understandable, time bound, and reasonably sized groups which are compatible and transferable with common database technologies. Each segment can be easily reviewed to determine if it is complete. This approach further enables alignment of time segments collected from multiple different systems and/or devices. Segments from multiple segments can be aligned using common events, common durations, or common aligned time basis between segments. For example, a low glucose level may occur both as a reading from a CGM and as an alert on a pump and segments from the CGM and the pump can therefore be aligned based on the low glucose level. Similarly, an exercise event or duration can be indicated on the pump with a temporary exercise basal rate or other indication and also be tracked on a fitness tracking device. Segments can be easily understood based on sequence, relative time, or user time and easy visualization can provide for searches such as, e.g., "all Mondays," based on user time. The relative time between segments is further understood and therefore translatable back to the user experience.

After data has been segmented and prior to displaying data, events that started prior to a given segment and carried into the segment need to be anticipated. This can be done by searching the previous segment for these events and/or structuring the event messages in such a way that the relative start time or duration is recorded at the end of the event. Similar approaches can be used for events that start during a given segment and do not end in that segment.

For events that span multiple segments due to date and/or time changes, the overall duration can be evaluated by incorporating the relative time difference between segments. For example, if an event is initiated, the event runs for an hour, the time is then changed forward 2 hours, the even runs for another hour, then the time is changed back one hour and the event runs for another hour and concludes, the total duration of the event can be determined to be three hours by looking at each segment. In contrast, if just the overall event is summarized without reviewing each segment, the event duration would appear to be 2 hours due to the time changes.

Figure 2:
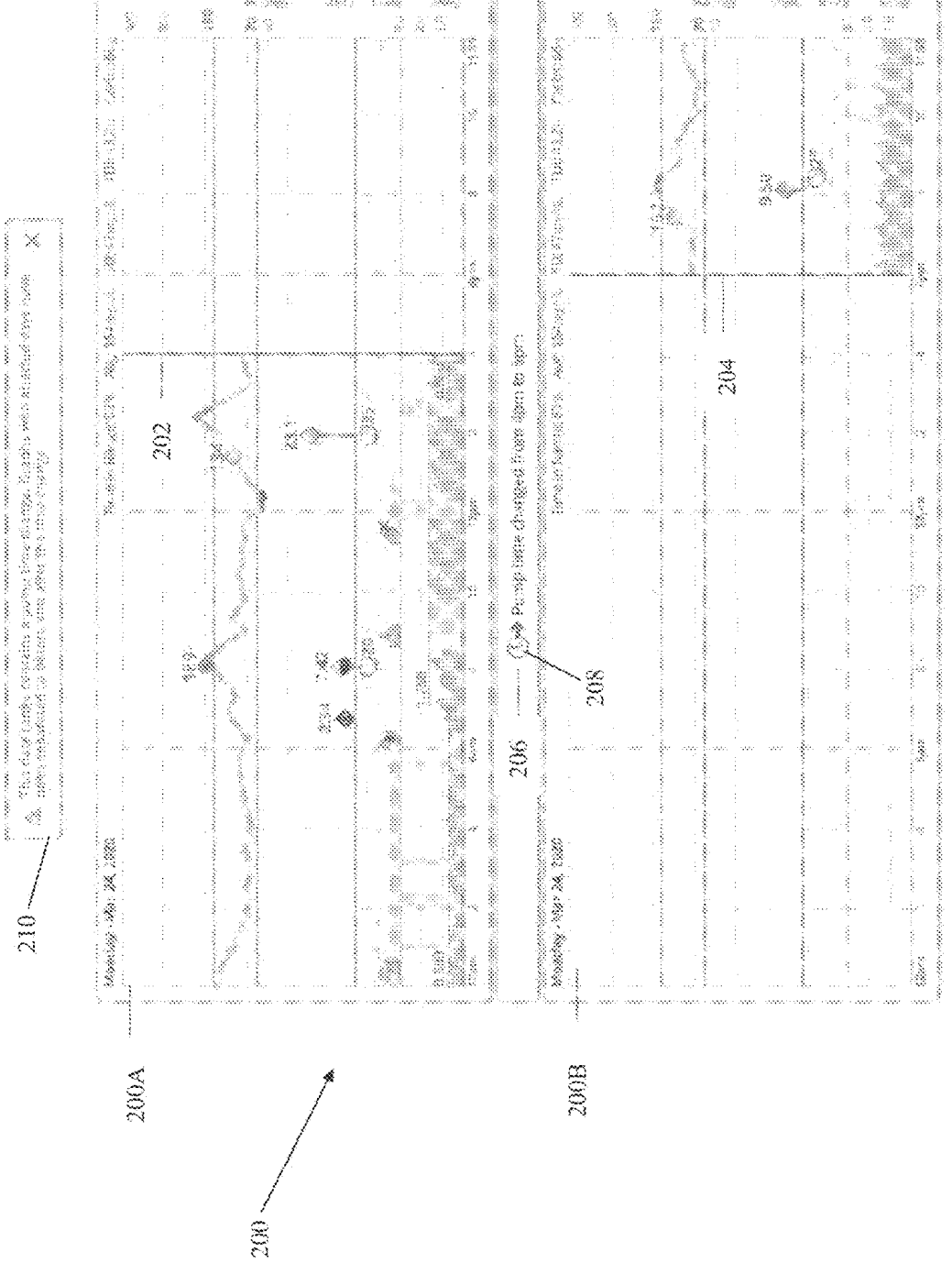
FIG. 2 depict a therapy timeline graph incorporating a time change according to an embodiment.

Referring now to FIG. 2, a therapy timeline graph 200 that incorporates a time change according to the disclosure is depicted. Therapy timeline graph 200 includes an initial time graph 200A and a time change graph 200B, each of which can include any or all of the elements described above with respect to FIG. 1. Initial time graph 200A displays data up to the point in time when the pump time was changed (for example by a user manually adjusting the pump time clock) and time change graph 200B is a new graph that displays data beginning at the new time and/or data following the time change. An initial time change indicator can be displayed to provide a clear indication to the user that data is no longer displayed on the initial time graph 200A. In the depicted embodiment, the initial time change indicator is provided in the form of a vertical bar 202 that extends across the entire data feed 200A at the point in time when the pump time was changed. A corresponding time change indictor 204 can be provided, e.g., in the form of a vertical bar extending across the entire data feed 200B, at the point in time that the pump was changed to in order to provide a clear indication that a new therapy feed is beginning from that point in time. Multiple time change indicators/bars can be displayed on a graph if multiple time changes occurred.

A time change info tile 206 can also be provided between the graphs to provide textual information explaining the time change to the user. For example, the depicted time change info tile 206 includes a time change icon 208 indicating whether the time change was forward (as in the depicted embodiment) or backward along with text informing the user of the exact time change from the previous time to the new time, e.g., "from 4 pm to 6 pm." In some embodiments if the new time or the previous time is outside of the displayed time/date range, the text can be a selectable link that will trigger a new date range display including the non-displayed data. A second link can be displayed when a large time change back occurs to enable the user to select and see the same date range with the previous set of data (timeline) that was overwritten by the time change. Timeline 200 can further include time change banner 210 when there is a time change within a selected date range to inform the user of the time change and that the graph is separated into a before time change graph 200A and after time change graph 200B.

Figure 3:
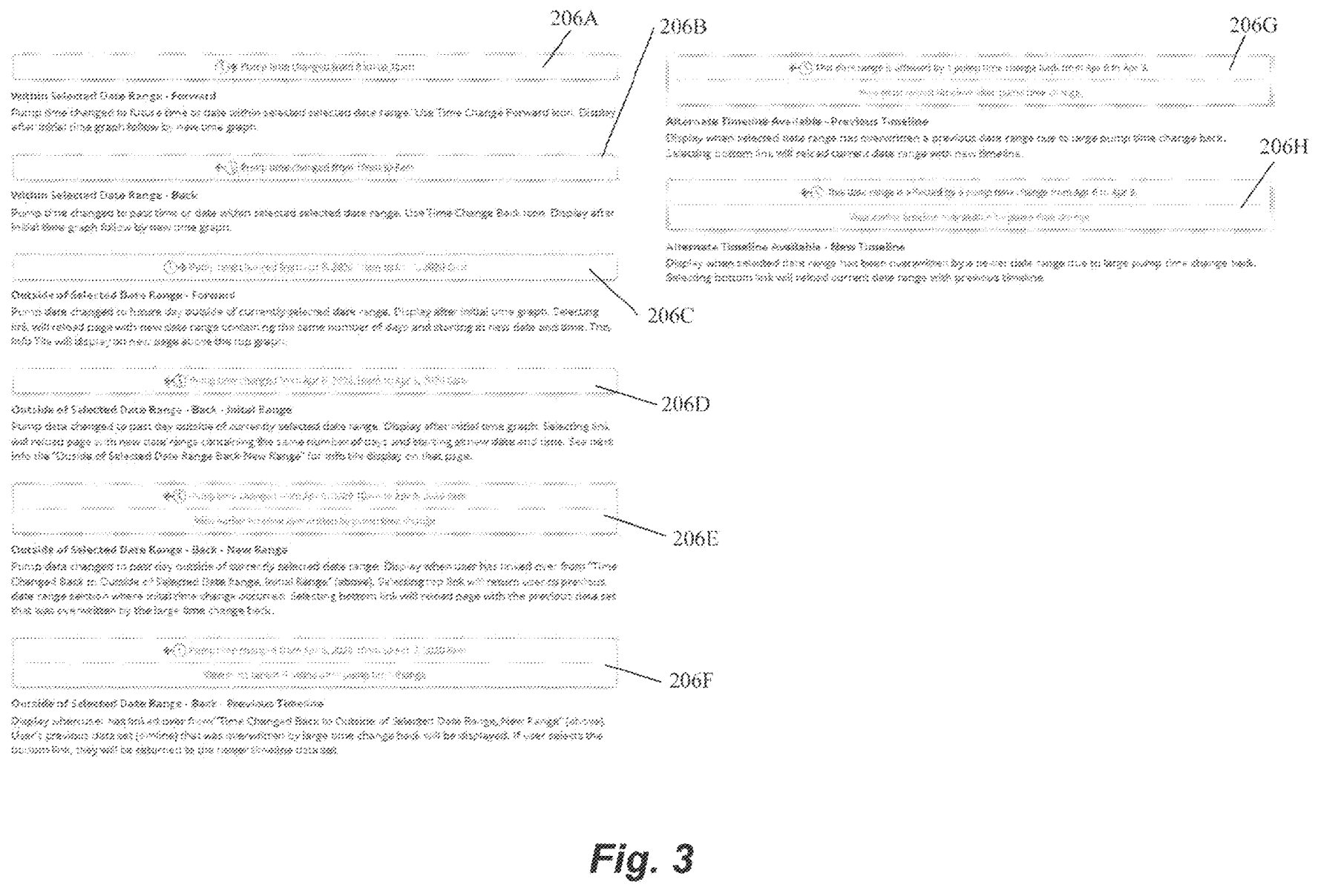

Referring now to FIG. 3, a plurality of time change info tiles 206 that can be displayed in various circumstances are depicted. Tiles 206A and 206B are similar to tile 206 depicted in FIG. 2 in that they represent a forward time change and a backward time change, respectively, within the currently selected date range. Tiles 206C and 206D can be depicted when the pump time and date had been changed outside of the currently selected data range. The appropriate tile 206C, 206D can be displayed on the initial time graph and selection of the link contained in the tile will reload the page with a new date range containing the same number of days and starting at the new date and time. Time change tile 206E can be displayed when the pump date is changed to a past day outside of the currently selected date range and the user has selected the link in info tile 206D to view the new date range. Selecting the top link in this tile 206E will return the user to the previous date range selection where the initial time change occurred and selecting the bottom link will reload the page with the previous data set that was overwritten by the large time change back. Time change tile 206F is displayed when the user has selected the link in info tile 206E to view the new date range. Selection of the top link in this tile 206F will display the previous timeline that was overwritten by the large time change and selection of the bottom link will return the user to the newer timeline data set. Time change tile 206G can be displayed when the selected data range has overwritten a previous date range due to a large time change backward. Selection of the bottom link in this time change tile 206G will reload the current date range with the new timeline. Time change tile 206H subsequently will be displayed and can be selected to reload the current date range with the previous timeline.

Figure 4B:
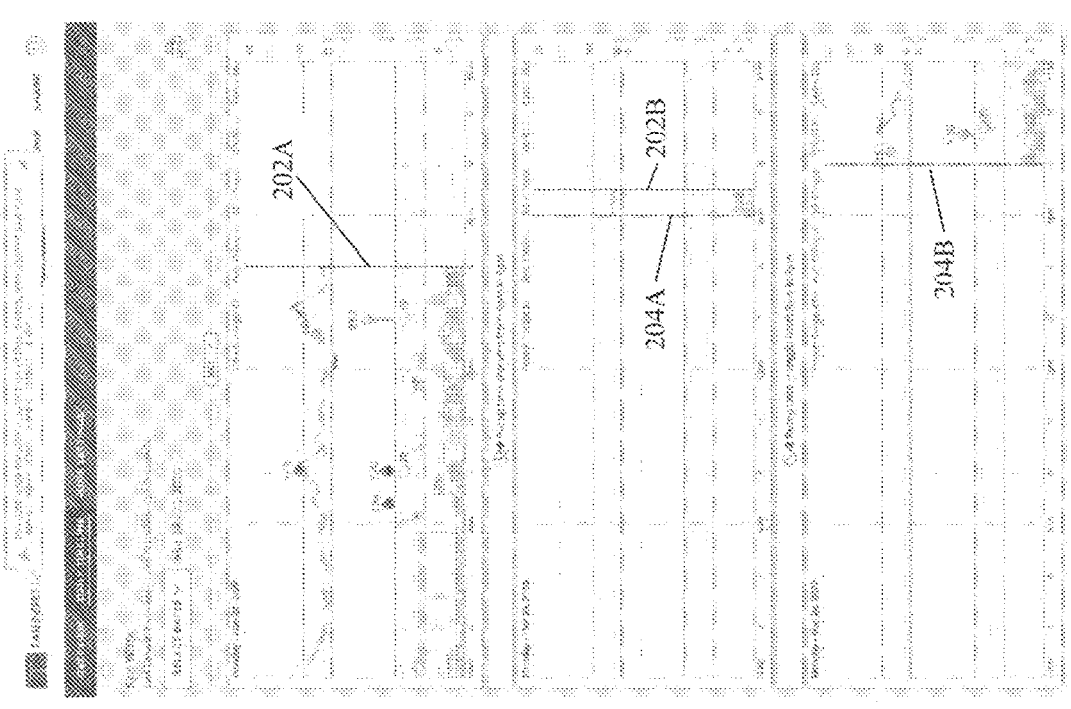
FIGS. 4A-4D depict therapy timeline graphs incorporating time changes according to embodiments.
Figure 4A:
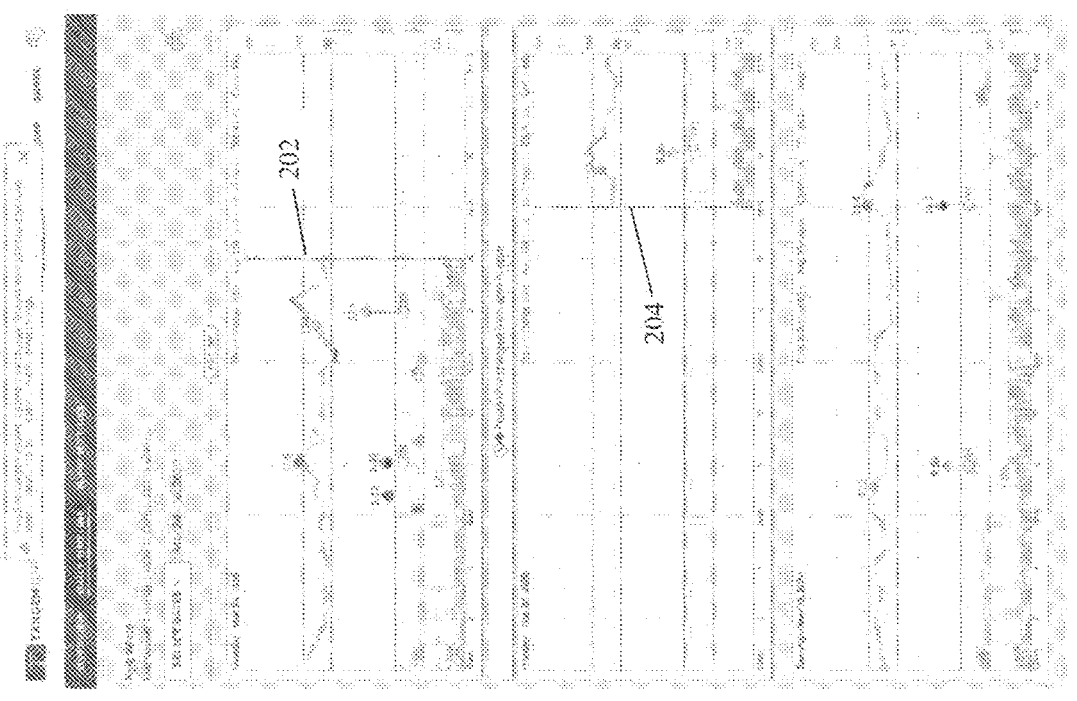
Figure 4C:
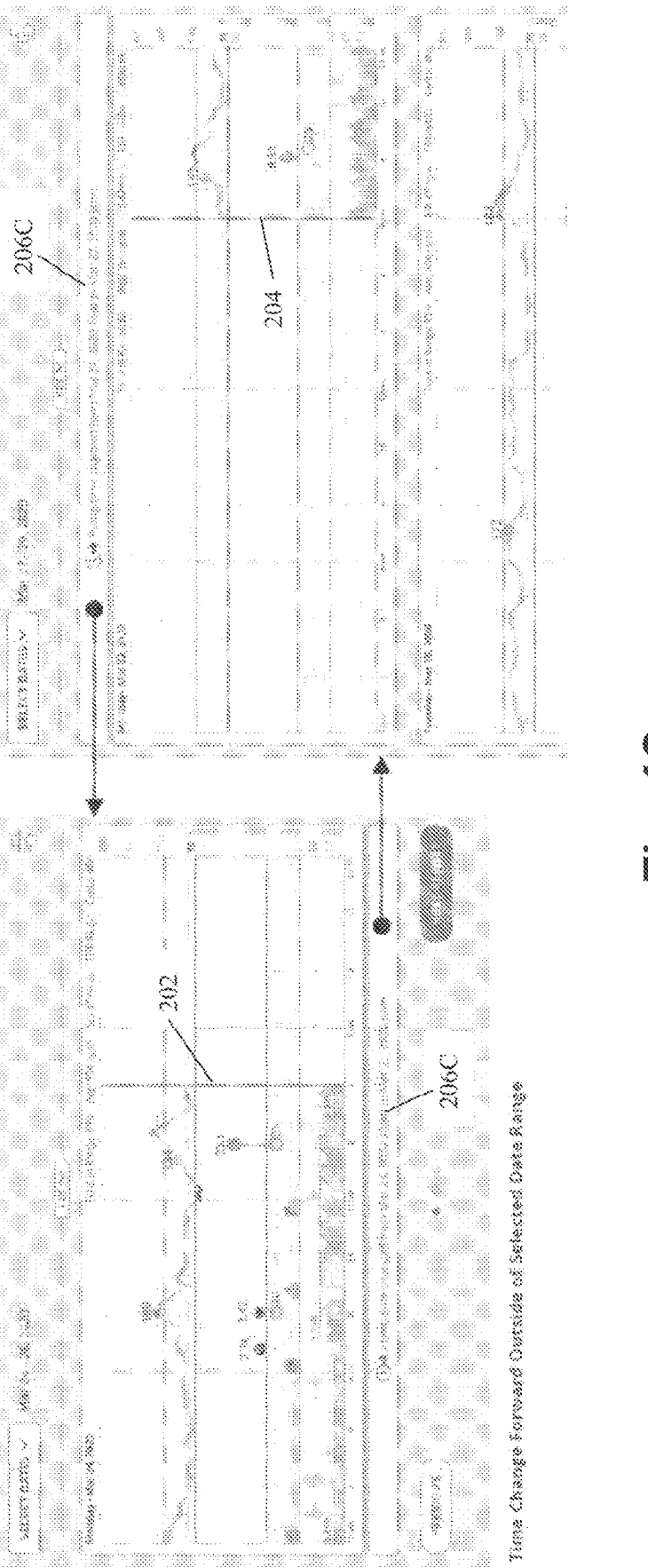
Figure 4D:
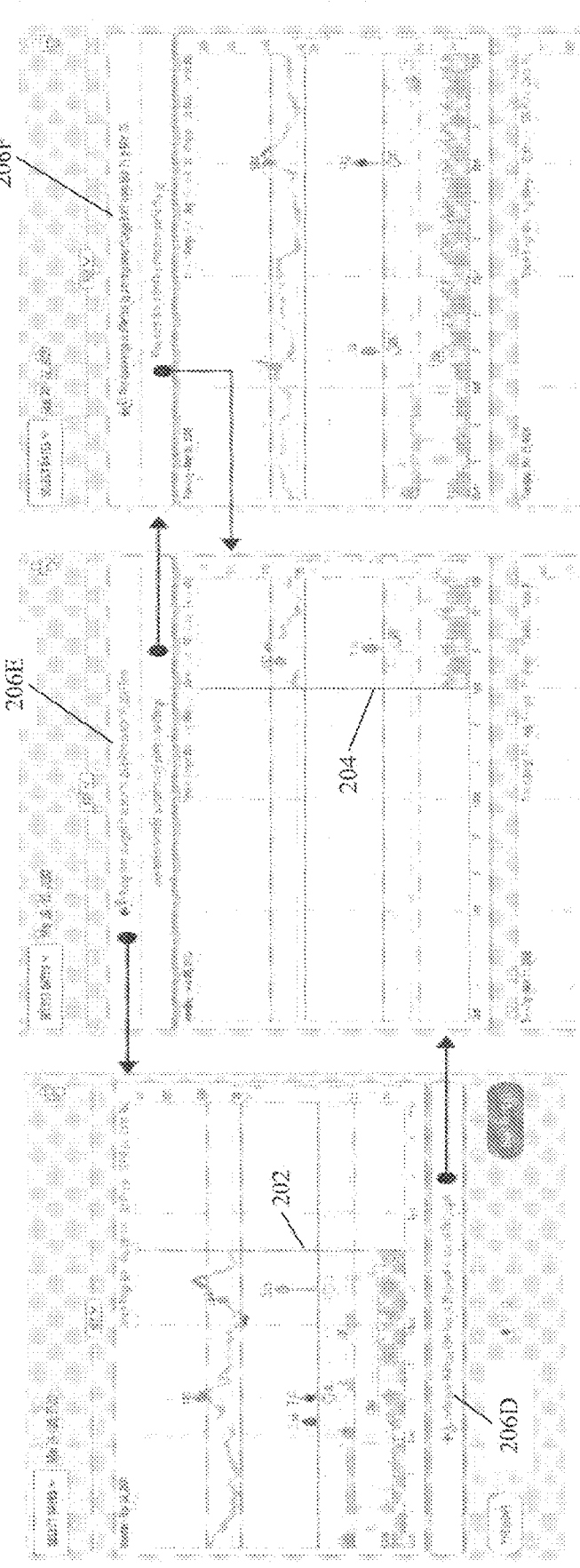

FIGS. 4A-4D depict various additional therapy timelines according to embodiments. FIG. 4A depicts a single time change within the selected date range with time change indicators 202, 204 such as the time change described above with respect to FIG. 2. The embodiment of FIG. 4B depicts first and second time changes within the selected date range with first 202A, 204A and second 202B, 204B time change indicators FIG. 4C depicts a single time change forward outside of the selected date range with time change indicators 202, 204 and time change info tiles 206C that are selectable to move between the different timelines. The therapy timelines in FIG. 4D can be displayed when there is a time change back outside of the selected range indicated by time change indicators 202, 204. Info tile 206D can be displayed on the initial graph and can be selected to display a therapy timeline with the new date and time. This updated timeline includes info tile 206E having links to both go back to the previous date range where the time change occurred and to reload the page with the previous dataset that was overwritten by the time change. This reloaded page then includes info tile 206F that can be selected to return to the previous timeline.

Although embodiments described herein may be discussed in the context of the controlled delivery of insulin, delivery of other medicaments, singly or in combination with one another or with insulin, including, for example, glucagon, pramlintide, etc., as well as other applications are also contemplated. Device and method embodiments discussed herein may be used for pain medication, chemotherapy, iron chelation, immunoglobulin treatment, dextrose or saline IV delivery, treatment of various conditions including, e.g., pulmonary hypertension, or any other suitable medical indication or application. Non-medical applications are also contemplated, including fitness tracking and meal logging applications.

With regard to the above detailed description, like reference numerals used therein may refer to like elements that may have the same or similar dimensions, materials, and configurations. While particular forms of embodiments have been illustrated and described, it will be apparent that various modifications can be made without departing from the spirit and scope of the embodiments herein. Accordingly, it is not intended that the invention be limited by the forgoing detailed description.

The entirety of each patent, patent application, publication, and document referenced herein is hereby incorporated by reference. Citation of the above patents, patent applications, publications and documents is not an admission that any of the foregoing is pertinent prior art, nor does it constitute any admission as to the contents or date of these documents.

Also incorporated herein by reference in their entirety are commonly owned U.S. Pat. Nos. 6,999,854; 8,133,197; 8,287,495; 8,408,421 8,448,824; 8,573,027; 8,650,937; 8,986,523; 9,173,998; 9,180,242; 9,180,243; 9,238,100; 9,242,043; 9,335,910; 9,381,271; 9,421,329; 9,486,171, 9,486,571; 9,492,608; 9,503,526; 9,555,186; 9,565,718; 9,603,995; 9,669,160; 9,715,327; 9,737,656; 9,750,871; 9,867,937; 9,867,953; 9,940,441, 9,993,595, 10,016,561; 10,201,656; 10,279,105; 10,279,106; 10,279,107, 10,357, 603; 10,357,606; 10,492,141; 10/541,987; 10,569,016; 10,736,037; 10,888,655; 10,994,077; 11,116,901; and 11,224,693 and commonly owned U.S. Patent Publication Nos. 2009/0287180; 2012/0123230; 2013/0053816; 2014/ 0276423; 2014/0276569; 2014/0276570, 2018/0071454;

2019/0240398; 2019/0307952; 2020/0206420, 2020/0261649; 2020/0306445; 2020/0329433; 2020/0368430, 2020/0372995; 2021/0001044; 2021/0113766; 2021/0154405; and 2021/0353857 and commonly owned U.S. patent application Ser. Nos. 17/368,968; 17/459,129; 17/517,885 and 17/573,705.

Modifications may be made to the foregoing embodiments without departing from the basic aspects of the technology. Although the technology may have been described in substantial detail with reference to one or more specific embodiments, changes may be made to the embodiments specifically disclosed in this application, yet these modifications and improvements are within the scope and spirit of the technology. The technology illustratively described herein may suitably be practiced in the absence of any element(s) not specifically disclosed herein. The terms and expressions which have been employed are used as terms of description and not of limitation and use of such terms and expressions do not exclude any equivalents of the features shown and described or portions thereof and various modifications are possible within the scope of the technology claimed. Although the present technology has been specifically disclosed by representative embodiments and optional features, modification and variation of the concepts herein disclosed may be made, and such modifications and variations may be considered within the scope of this technology.

The invention claimed is:

1. A system for organizing and presenting diabetes therapy events on a graphical user interface, comprising a computing device configured for:
  obtaining data relevant to diabetes therapy from a plurality of different sources;
  segmenting the data relevant to diabetes therapy data into segments for each of the plurality of sources, wherein each segment for each source represents a continuous period of data for the source and additional segments are created for each source when there has been a data disruption on the source;
  aligning segments from each source with segments from other sources with respect to real time; and
  displaying a therapy timeline including data from one or more segments of the plurality of sources on a graphical user interface, the therapy timeline displaying aligned segments over a predetermined time period with the data from the plurality of sources overlaid on the timeline at a time that events recorded by the plurality of sources occurred.

2. The system of claim 1, wherein aligning segments from each source with segments from other sources with respect to real time includes identifying common events occurring in segments from different sources and aligning the segments by aligning the common events.

3. The system of claim 1, wherein creating additional segments when there has been a data disruption includes creating an additional segment when there has been a time change on the source.

4. The system of claim 1, wherein creating additional segments when there has been a data disruption includes creating an additional segment when there is a period with no data received on the source.

5. The system of claim 1, wherein displaying events from the plurality of sources on the timeline includes displaying icons representing particular types of events on the therapy timeline.

6. The system of claim 1, wherein the computing device is configured for receiving user input selecting an icon displayed on the therapy timeline and displaying further details regarding the event represented by the icon upon receiving the user input.

7. The system of claim 1, wherein to display a therapy timeline includes displaying a glucose level data feed depicting a user's glucose levels over time for the predetermined time period displayed on the therapy timeline.

8. The system of claim 7, wherein the therapy timeline further includes a graphical representation of insulin delivered to the user during the predetermined time period.

9. The system of claim 7, wherein the events displayed on the therapy timeline include one or more of sleep, exercise, and infusion pump events.

10. The system of claim 1, wherein the computing device is configured for obtaining data relevant to diabetes therapy from a plurality of different sources includes obtaining data from an infusion pump, a continuous glucose monitor, an insulin pen, a smartphone, a smartwatch, a remote control device for an infusion pump and/or an activity monitoring device.

11. A system for organizing and presenting diabetes therapy events on a graphical user interface, comprising a computing device configured for:
  obtaining data relevant to diabetes therapy from a plurality of different sources including an infusion pump;
  displaying on a graphical user interface a therapy timeline including data from the plurality of sources over a predetermined time period with the data from the plurality of sources overlaid on the therapy timeline at a time that events from the plurality of sources occurred;
  determining that a pump time was changed on the infusion pump;
  ceasing displaying data on the therapy timeline at a time when the pump time was changed on the infusion pump and displaying a time change indicator on the therapy timeline at the time when the pump time was changed on the infusion pump; and
  displaying on the graphical user interface a time change therapy timeline, the time change therapy timeline displaying the data from the plurality of sources beginning at a time to which the pump time was changed, the time change therapy timeline include a time change indicator at the time to which the pump time was changed.

12. The system of claim 11, wherein the therapy timeline and the time change therapy timeline are aligned with each other on the graphical user interface with respect to time.

13. The system of claim 12, wherein the therapy timeline and the time change therapy timeline are vertically aligned on the graphical user interface.

14. The system of claim 11, wherein the time change indicator on the therapy timeline is a solid line extending across the therapy timeline at the time when the pump time was changed on the infusion pump.

15. The system of claim 11, wherein the time change indicator on the time change therapy timeline is a solid line extending across the time change therapy timeline at the time to which the pump time was changed.

16. The system of claim 11, wherein the computing device is configured for displaying a time change info tile on the graphical user interface.

17. The system of claim 16, wherein displaying the time change info tile on the graphical user interface includes displaying textual details regarding the time change.

18. The system of claim 16, wherein displaying the time change info tile on the graphical user interface includes displaying an icon representing the time change.

19. The system of claim 16, wherein if the time change therapy timeline is not displayed on a same screen of the graphical user interface as the therapy timeline, selection of the time change info tile causes the time change therapy timeline to be displayed on the graphical user interface.

20. The system of claim 16, wherein the computing device is configured for displaying a time change banner above the therapy timeline and the time change therapy timeline when the therapy timeline and time change therapy timeline are displayed on a same screen of the graphical user interface, the time change banner indicating that the screen includes a time change.

\* \* \* \* \*